(12) United States Patent
Gross

(10) Patent No.: US 11,484,700 B1
(45) Date of Patent: Nov. 1, 2022

(54) MECHANICAL TREATMENT OF HEART FAILURE

(71) Applicant: RAINBOW MEDICAL LTD., Herzliya (IL)

(72) Inventor: Yossi Gross, Moshav Mazor (IL)

(73) Assignee: YOSSI GROSS, Moshav Mazor (IL)

( * ) Notice: Subject to any disclaimer, the term of this patent is extended or adjusted under 35 U.S.C. 154(b) by 0 days.

(21) Appl. No.: 17/509,495

(22) Filed: Oct. 25, 2021

(51) Int. Cl.
| | |
|---|---|
| A61M 60/806 | (2021.01) |
| A61M 60/122 | (2021.01) |
| A61F 2/82 | (2013.01) |
| A61M 60/871 | (2021.01) |
| A61M 60/861 | (2021.01) |
| A61M 60/232 | (2021.01) |

(52) U.S. Cl.
CPC ............. *A61M 60/806* (2021.01); *A61F 2/82* (2013.01); *A61M 60/122* (2021.01); *A61M 60/232* (2021.01); *A61M 60/861* (2021.01); *A61M 60/871* (2021.01)

(58) Field of Classification Search
CPC ............. A61M 60/806; A61M 60/122; A61M 60/232; A61M 60/861; A61M 60/871; A61F 2/82
See application file for complete search history.

(56) References Cited

U.S. PATENT DOCUMENTS

| | | |
|---|---|---|
| 4,546,759 A | 10/1985 | Solar |
| 4,994,017 A | 2/1991 | Yozu |
| 4,994,078 A | 2/1991 | Jarvik |
| 5,139,517 A | 8/1992 | Corral |
| 5,762,599 A | 6/1998 | Sohn |
| 5,810,757 A | 9/1998 | Sweezer, Jr. et al. |
| 5,891,012 A | 4/1999 | Downey et al. |
| 6,332,893 B1 | 12/2001 | Mortier et al. |
| 6,406,422 B1 | 6/2002 | Landesberg |

(Continued)

FOREIGN PATENT DOCUMENTS

| | | |
|---|---|---|
| WO | 2004/066805 | 8/2004 |
| WO | 2004/108191 | 12/2004 |

(Continued)

OTHER PUBLICATIONS

Généreux, Philippe, "AltaValve™", CRT19 Mar. 2019 Presentation, 21 pages total.

*Primary Examiner* — Catherine M Voorhees
*Assistant Examiner* — Roland Dinga
(74) *Attorney, Agent, or Firm* — Sughrue Mion, PLLC

(57) ABSTRACT

Apparatus is provided for treating heart failure, the apparatus including one or more propeller blades and a controller, which is configured to rotate the one or more propeller blades to produce continuous non-pulsatile blood flow not synchronized with a cardiac cycle of a subject. An intra-atrial anchor includes a stent surrounding the one or more propeller blades. The intra-atrial anchor is coupled to the one or more propeller blades and configured to be anchored in a left atrium of the subject so as to position the one or more propeller blades in the left atrium oriented such that the one or more propeller blades, when rotated by the controller, draw blood from the left atrium and expel the blood in the left atrium toward a mitral valve, thereby increasing atrial pressure above the mitral valve. Other embodiments are also described.

22 Claims, 3 Drawing Sheets

(56) References Cited

U.S. PATENT DOCUMENTS

| | | |
|---|---|---|
| 6,432,039 B1 | 8/2002 | Wardle |
| 7,159,593 B2 | 1/2007 | McCarthy et al. |
| 7,404,824 B1 | 7/2008 | Webler et al. |
| 7,431,692 B2 | 10/2008 | Zollinger et al. |
| 7,476,200 B2 | 1/2009 | Tal |
| 7,483,743 B2 | 1/2009 | Mann et al. |
| 7,635,329 B2 | 12/2009 | Goldfarb et al. |
| 7,862,501 B2 | 1/2011 | Woodard |
| 7,927,268 B1 | 4/2011 | St Germain et al. |
| 8,057,493 B2 | 11/2011 | Goldfarb et al. |
| 8,147,542 B2 | 4/2012 | Maisano et al. |
| 8,790,394 B2 | 7/2014 | Miller et al. |
| 8,876,850 B1 | 11/2014 | Vollmers et al. |
| 9,232,999 B2 | 1/2016 | Maurer et al. |
| 9,517,129 B2 | 12/2016 | Wilson et al. |
| 9,545,305 B2 | 1/2017 | Wilson et al. |
| 9,833,316 B2 | 12/2017 | Wilson et al. |
| 10,039,874 B2 | 8/2018 | Schwammenthal et al. |
| 10,098,992 B2 | 10/2018 | Van Dort et al. |
| 10,286,131 B2 | 5/2019 | Sohn et al. |
| 10,517,719 B2 | 12/2019 | Miller et al. |
| 10,610,360 B2 | 4/2020 | Reich et al. |
| 10,722,631 B2 | 7/2020 | Salahieh et al. |
| 10,751,184 B2 | 8/2020 | Reich et al. |
| 10,820,998 B2 | 11/2020 | Man et al. |
| 10,888,644 B2 | 1/2021 | Ratz et al. |
| 10,973,966 B2 | 4/2021 | Sohn et al. |
| 11,051,940 B2 | 7/2021 | Metchik et al. |
| 2002/0169360 A1 | 11/2002 | Taylor et al. |
| 2002/0173742 A1 | 11/2002 | Keren et al. |
| 2003/0216801 A1 | 11/2003 | Tweden et al. |
| 2004/0111006 A1 | 6/2004 | Alfemess et al. |
| 2005/0148925 A1 | 7/2005 | Rottenberg et al. |
| 2005/0154250 A1 | 7/2005 | Aboul-hosn et al. |
| 2005/0165344 A1 | 7/2005 | Dobak, III |
| 2005/0256566 A1 | 11/2005 | Gabbay |
| 2006/0064059 A1 | 3/2006 | Gelfand et al. |
| 2006/0155158 A1* | 7/2006 | Aboul-Hosn ......... A61M 60/82 600/16 |
| 2006/0206029 A1 | 9/2006 | Yair |
| 2006/0241745 A1 | 10/2006 | Solem |
| 2007/0073218 A1 | 3/2007 | Lau et al. |
| 2007/0299296 A1 | 12/2007 | Vaska |
| 2008/0004485 A1 | 1/2008 | Moreschi |
| 2008/0207986 A1 | 8/2008 | Choy |
| 2008/0269871 A1* | 10/2008 | Eli ................. A61F 2/0108 623/1.42 |
| 2010/0023117 A1 | 1/2010 | Yoganathan et al. |
| 2010/0057192 A1 | 3/2010 | Celermajer |
| 2010/0298929 A1 | 11/2010 | Thornton et al. |
| 2011/0112632 A1 | 5/2011 | Chau et al. |
| 2011/0218480 A1 | 9/2011 | Rottenberg et al. |
| 2011/0306916 A1 | 12/2011 | Nitzan et al. |
| 2012/0059213 A1 | 3/2012 | Spence |
| 2012/0143320 A1 | 6/2012 | Eliasen et al. |
| 2014/0213959 A1 | 7/2014 | Nitzan et al. |
| 2015/0335801 A1 | 11/2015 | Faman et al. |
| 2016/0015877 A1 | 1/2016 | Guerrero et al. |
| 2016/0166747 A1 | 6/2016 | Frazier et al. |
| 2017/0136162 A1 | 5/2017 | Van Dort et al. |
| 2017/0231766 A1 | 8/2017 | Hariton et al. |
| 2017/0325949 A1 | 11/2017 | Rodgers et al. |
| 2018/0001004 A1 | 1/2018 | Sohn et al. |
| 2018/0318482 A1* | 11/2018 | Timms ................ A61M 60/148 |
| 2020/0188101 A1 | 6/2020 | Chambers |
| 2021/0022858 A1 | 1/2021 | Miller et al. |
| 2021/0121679 A1* | 4/2021 | Mohl ................. A61M 60/405 |

FOREIGN PATENT DOCUMENTS

| | | |
|---|---|---|
| WO | 2007/132449 | 11/2007 |
| WO | 2007/149562 | 12/2007 |
| WO | 2008141325 A1 | 11/2008 |
| WO | 2010/128501 | 11/2010 |
| WO | 2014/203078 | 12/2014 |
| WO | 2015/177793 | 11/2015 |
| WO | 2016/113743 | 7/2016 |
| WO | 2020/081481 | 4/2020 |

\* cited by examiner

MECHANICAL TREATMENT OF HEART FAILURE

FIELD OF THE APPLICATION

The present invention relates generally to techniques for treatment of heart failure, and specifically to techniques for mechanical treatment of heart failure.

BACKGROUND OF THE APPLICATION

In diastolic heart failure, the left ventricle does not fill properly with blood during diastole, reducing the amount of blood pumped to the body. Diastolic heart failure is also known as heart failure with preserved ejection fraction (HFpEF). Diastolic heart failure may or may not be accompanied by mitral regurgitation.

In systolic hearth failure, the left ventricle does not contract with sufficient force to push enough blood into circulation. Systolic heart failure is also known as heart failure with reduced ejection fraction (HFrEF).

Both diastolic and systolic heart failure may cause pulmonary edema, also known as pulmonary congestion, which is the accumulation of liquid in the lungs. Cardiogenic pulmonary edema is pulmonary edema that is caused by the failure of the left ventricle to remove blood adequately from the pulmonary circulation.

SUMMARY OF THE APPLICATION

Some embodiments of the present invention provide apparatus for treating heart failure, the apparatus comprising one or more propeller blades, a controller, and an intra-atrial anchor, which typically comprises a stent surrounding the one or more propeller blades. The controller is configured to rotate the one or more propeller blades to produce continuous non-pulsatile blood flow not synchronized with a cardiac cycle of a subject. The intra-atrial anchor is coupled to the one or more propeller blades and configured to be anchored in the left atrium so as to position the one or more propeller blades in the left atrium oriented such that the one or more propeller blades, when rotated by the controller, draw blood from the left atrium and expel the blood in the left atrium toward the mitral valve, thereby increasing atrial pressure above the mitral valve. It is noted that the one or more propeller blades expel the blood in the left atrium, rather than in the left ventricle (although the blood subsequently flows to the left ventricle when the mitral valve is open during the cardiac cycle).

The increased pressure above the mitral valve augments the left-ventricle filling pressure, thereby increasing filling of the left ventricle during diastole. Rotation of the one or more propeller blades gradually builds up pressure above the mitral valve, beginning during ventricular systole, such that blood flow through the mitral valve is enhanced when the mitral valve opens early in ventricular diastole.

For some applications, the controller is configured to rotate the one or more propeller blades so as to generate a pressure increase of 10-30 mmHg between (a) an inferior area of the left atrium between the one or more propeller blades and the mitral valve and (b) a superior area of the left atrium between the one or more propeller blades and the left atrial roof. This fairly low pressure increase generally does not result in meaningful backflow.

For some applications, the controller is configured to rotate the one or more blades at a speed of at least 100 rpm (e.g., at least 300 rpm, such as at least 500 rpm), no more than 2000 rpm (e.g., no more than 1500 rpm, such as no more than 1200 rpm) 1000 rpm, and/or 100-2000 rpm, e.g., 300-1500 rpm, such as 300-1200 rpm, e.g., 500-1200 rpm, such as 1000 rpm.

Optionally, the one or more propeller blades may be configured to be toward a central longitudinal axis of the apparatus to provide radial compression for delivery to the left atrium, such as transcatheter delivery. (For example, the one or more propeller blades may be hingedly coupled to the rotating shaft.) The one or more propeller blades may be configured to expand centrifugally when rotated, and/or one or more springs may be provided to cause the blades to expand radially.

There is therefore provided, in accordance with an Inventive Concept 1 of the present invention, apparatus for treating heart failure, the apparatus including:

one or more propeller blades;

a controller, which is configured to rotate the one or more propeller blades to produce continuous non-pulsatile blood flow not synchronized with a cardiac cycle of a subject; and an intra-atrial anchor, which includes a stent surrounding the one or more propeller blades, and which is coupled to the one or more propeller blades and configured to be anchored in a left atrium of the subject so as to position the one or more propeller blades in the left atrium oriented such that the one or more propeller blades, when rotated by the controller, draw blood from the left atrium and expel the blood in the left atrium toward a mitral valve, thereby increasing atrial pressure above the mitral valve.

Inventive Concept 2. The apparatus according to Inventive Concept 1, wherein the controller is configured to rotate the one or more propeller blades so as to generate a pressure increase of 10-30 mmHg between (a) an inferior area of the left atrium between the one or more propeller blades and the mitral valve and (b) a superior area of the left atrium between the one or more propeller blades and the left atrial roof.

Inventive Concept 3. The apparatus according to Inventive Concept 1, wherein the controller is configured to rotate one or more propeller blades at a speed of no more than 2000 rpm.

Inventive Concept 4. The apparatus according to Inventive Concept 3, wherein the controller is configured to rotate one or more propeller blades at a speed of no more than 1500 rpm.

Inventive Concept 5. The apparatus according to Inventive Concept 1, wherein a circle defined by respective radially-outer ends of the one or more propeller blades when rotating has a diameter of 4-6 cm.

Inventive Concept 6. The apparatus according to Inventive Concept 1, further including a motor, wherein the controller is configured to rotate the one or more propeller blades by controlling the motor.

Inventive Concept 7. The apparatus according to Inventive Concept 1, wherein the one or more propeller blades are configured to be folded toward a central longitudinal axis of the apparatus to provide radial compression for delivery to the left atrium, and wherein the one or more propeller blades are configured to expand centrifugally when rotated.

Inventive Concept 8. The apparatus according to Inventive Concept 1, wherein the apparatus includes 2-5 propeller blades.

Inventive Concept 9. The apparatus according to Inventive Concept 1, further including a power source.

Inventive Concept 10. The apparatus according to Inventive Concept 9, wherein the power source is fully implantable.

Inventive Concept 11. The apparatus according to Inventive Concept 1, wherein the intra-atrial anchor is configured be disposed entirely within the left atrium when anchored therein.

Inventive Concept 12. The apparatus according to Inventive Concept 1, wherein the stent is sized and shaped to engage or contact a substantial portion of an interior surface of the left atrium.

Inventive Concept 13. The apparatus according to any one of Inventive Concepts 1-12, wherein the stent is shaped as a cage surrounding the one or more propeller blades.

Inventive Concept 14. The apparatus according to Inventive Concept 13, wherein the cage is contractible during atrial contraction.

Inventive Concept 15. The apparatus according to any one of Inventive Concepts 1-12, wherein the stent is shaped generally as a complete or partial sphere.

Inventive Concept 16. The apparatus according to Inventive Concept 15, wherein the one or more propeller blades are disposed generally in a plane at or near an equator of the complete or partial sphere.

Inventive Concept 17. The apparatus according to any one of Inventive Concepts 1-12, wherein the one or more propeller blades and the stent are radially compressible for transcatheter delivery.

Inventive Concept 18. A system including the apparatus according to Inventive Concept 17, the system further including one or more sheaths in which the one or more propeller blades and the stent are disposed radially compressed for transcatheter delivery.

Inventive Concept 19. The system according to Inventive Concept 18, wherein the one or more propeller blades are disposed in the one or more sheaths folded toward a central longitudinal axis of the apparatus.

Inventive Concept 20. The system according to Inventive Concept 19, wherein the apparatus includes a rotating shaft, wherein the one or more propeller blades radiate from the rotating shaft when rotated, and wherein the one or more propeller blades are directly or indirectly hingedly coupled to the rotating shaft.

Inventive Concept 21. The system according to Inventive Concept 19, wherein the apparatus includes a rotating shaft and an intra-atrial housing disposed at least partially within the stent, wherein the rotating shaft extends distally from the intra-atrial housing, wherein the one or more propeller blades radiate from the rotating shaft when rotated, and wherein the one or more propeller blades, when radially compressed, extend distally from the rotating shaft in a direction away from the intra-atrial housing.

There is further provided, in accordance with an Inventive Concept 22 of the present invention, a method of treating heart failure, including:

anchoring a stent of an intra-atrial anchor of an apparatus in a left atrium of a subject diagnosed as suffering from heart failure so as to position one or more propeller blades, which are surrounded by the stent, in the left atrium oriented such that the one or more propeller blades, when rotated, draw blood from the left atrium and expel the blood in the left atrium toward a mitral valve, thereby increasing atrial pressure above the mitral valve; and activating a controller to rotate the one or more propeller blades to produce continuous non-pulsatile blood flow not synchronized with a cardiac cycle of the subject.

Inventive Concept 23. The method according to Inventive Concept 22, wherein anchoring the intra-atrial anchor in the left atrium includes anchoring the intra-atrial anchor in the left atrium of the subject diagnosed as suffering from heart failure without mitral regurgitation.

Inventive Concept 24. The method according to Inventive Concept 22, wherein anchoring the intra-atrial anchor in the left atrium includes anchoring the intra-atrial anchor in the left atrium of the subject diagnosed as suffering from pulmonary edema, and wherein activating the controller includes activating the controller to rotate the one or more propeller blades to lower pressure at orifices of pulmonary veins, thereby treating the pulmonary edema.

Inventive Concept 25. The method according to Inventive Concept 22, wherein activating the controller includes activating the controller to rotate the one or more propeller blades so as to generate a pressure increase of 10-30 mmHg between (a) an inferior area of the left atrium between the one or more propeller blades and the mitral valve and (b) a superior area of the left atrium between the one or more propeller blades and the left atrial roof.

Inventive Concept 26. The method according to Inventive Concept 22, wherein activating the controller includes activating the controller to rotate one or more propeller blades at a speed of no more than 2000 rpm.

Inventive Concept 27. The method according to Inventive Concept 26, wherein activating the controller includes activating the controller to rotate one or more propeller blades at a speed of no more than 1500 rpm.

Inventive Concept 28. The method according to Inventive Concept 22, wherein anchoring the intra-atrial anchor in the left atrium includes disposing the intra-atrial anchor entirely within the left atrium.

Inventive Concept 29. The method according to Inventive Concept 22, wherein anchoring the intra-atrial anchor includes anchoring the intra-atrial anchor in the left atrium such that the stent engages or contacts a substantial portion of an interior surface of the left atrium.

Inventive Concept 30. The method according to Inventive Concept 22, wherein the one or more propeller blades are configured to be folded toward a central longitudinal axis of the apparatus to provide radial compression for delivery to the left atrium, and wherein the one or more propeller blades are configured to expand centrifugally when rotated.

Inventive Concept 31. The method according to Inventive Concept 22, wherein the stent is shaped as a cage surrounding the one or more propeller blades.

Inventive Concept 32. The method according to Inventive Concept 31, wherein the cage is contractible during atrial contraction.

Inventive Concept 33. The method according to Inventive Concept 22, wherein the stent is shaped generally as a complete or partial sphere.

Inventive Concept 34. The method according to Inventive Concept 33, wherein the one or more propeller blades are disposed generally in a plane at or near an equator of the complete or partial sphere.

Inventive Concept 35. The method according to Inventive Concept 22, wherein anchoring the intra-atrial anchor includes delivering, in a transcatheter procedure, the one or more propeller blades and the stent to the left atrium while disposed radially compressed in one or more sheaths.

Inventive Concept 36. The method according to Inventive Concept 35, wherein delivering includes delivering the one or more propeller blades and the stent to the left atrium while the one or more propeller blades are disposed in the one or more sheaths folded toward a central longitudinal axis of the apparatus.

Inventive Concept 37. The method according to Inventive Concept 36, wherein the apparatus includes a rotating shaft, wherein the one or more propeller blades radiate from the rotating shaft when rotated, and wherein the one or more propeller blades are directly or indirectly hingedly coupled to the rotating shaft.

Inventive Concept 38. The method according to Inventive Concept 36, wherein the apparatus includes a rotating shaft and an intra-atrial housing disposed at least partially within the stent, wherein the rotating shaft extends distally from the intra-atrial housing, wherein the one or more propeller blades radiate from the rotating shaft when rotated, and wherein the one or more propeller blades, when radially compressed, extend distally from the rotating shaft in a direction away from the intra-atrial housing.

The present invention will be more fully understood from the following detailed description of embodiments thereof, taken together with the drawings, in which:

DETAILED DESCRIPTION OF APPLICATIONS

Figure 1A:
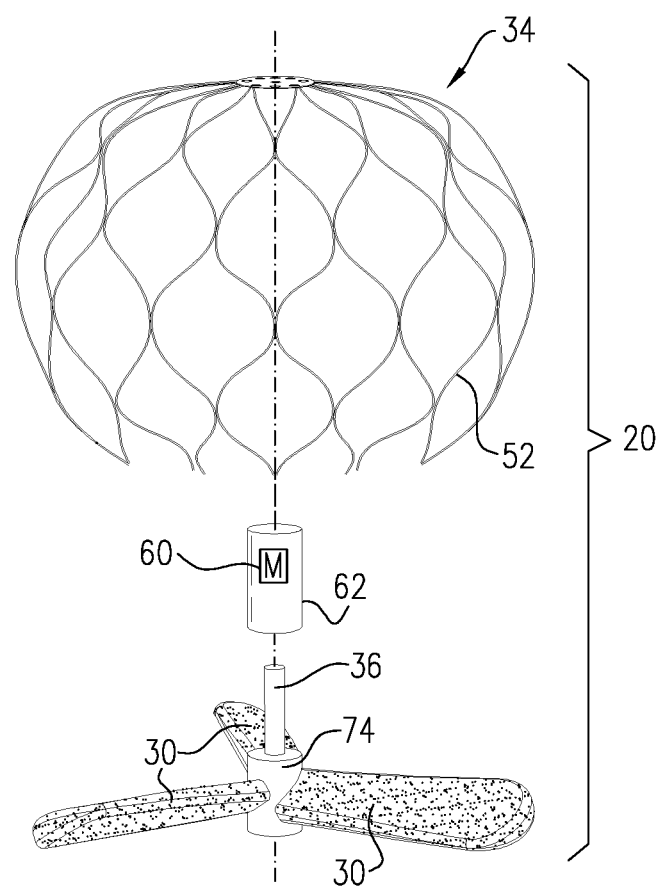
FIGS. 1A-B are schematic illustrations of apparatus for treating heart failure, in accordance with an application of the present invention.
Figure 1B:
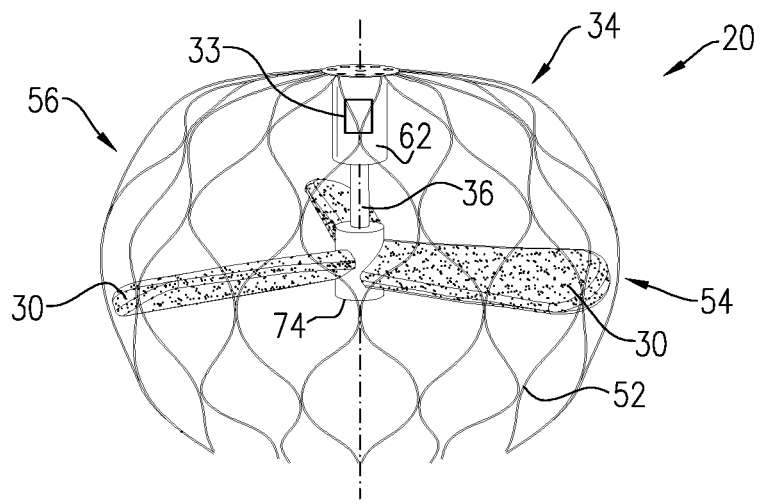
Figure 2A:
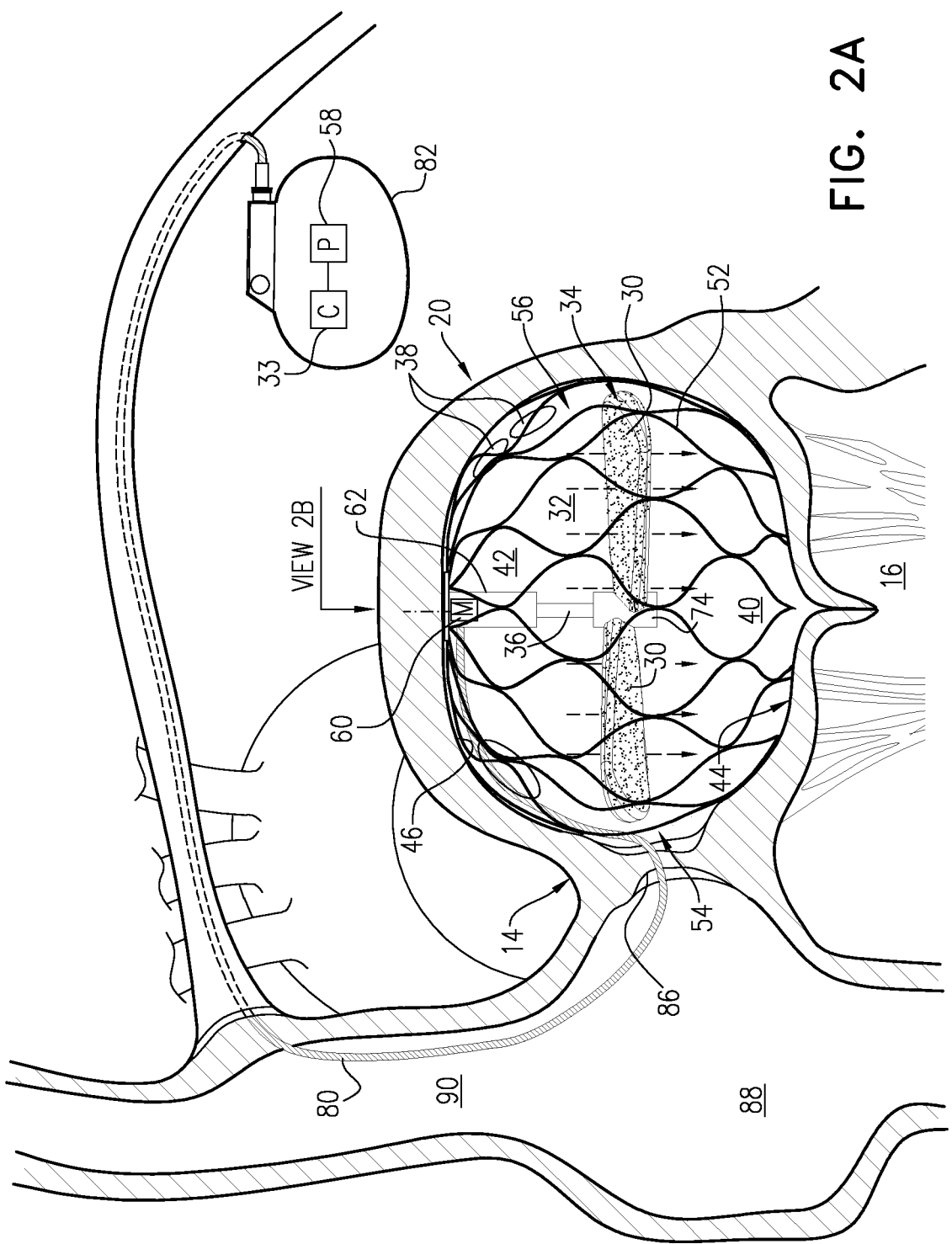
FIGS. 2A-B are schematic illustrations of the apparatus of FIGS. 1A-B anchored in a left atrium, in accordance with an application of the present invention.
Figure 2B:
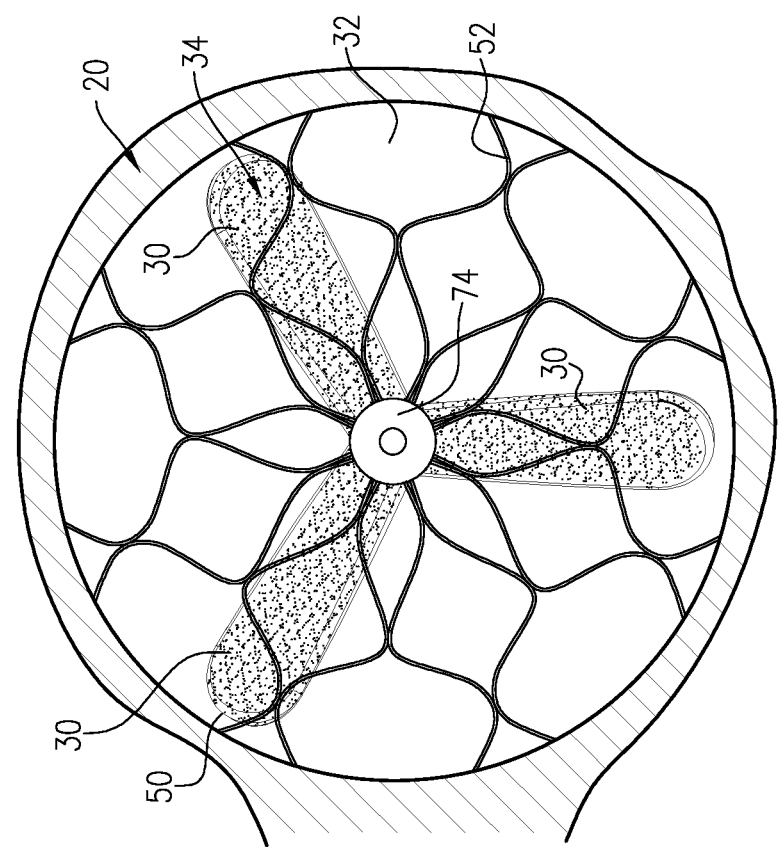

FIGS. 1A-B are schematic illustrations of apparatus for treating heart failure, in accordance with an application of the present invention. Reference is also made to FIGS. 2A-B, which are schematic illustrations of apparatus 20 anchored in a left atrium 32 of a heart 14, in accordance with an application of the present invention. Apparatus 20 is typically implanted in a subject diagnosed as suffering from heart failure (either diastolic or systolic), with or without mitral regurgitation. The subject may also suffer from pulmonary edema, such as cardiogenic pulmonary edema.

Apparatus 20 comprises:
one or more propeller blades 30;
a controller 33, which is configured to rotate the one or more propeller blades 30 to produce continuous non-pulsatile blood flow not synchronized with a cardiac cycle of a subject; and
an intra-atrial anchor 34, which is coupled to the one or more propeller blades 30 and configured to be anchored in left atrium 32 so as to position the one or more propeller blades 30 in left atrium 32 oriented such that the one or more propeller blades 30, when rotated by controller 33, draw blood from left atrium 32 and expel the blood in left atrium 32 toward a mitral valve 44 of heart 14, as indicated schematically in FIG. 2A, thereby increasing atrial pressure above mitral valve 44.

Controller 33 is thus configured to rotate the one or more propeller blades 30 to push the blood in an inferior direction, i.e., in a direction toward mitral valve 44.

For some applications, apparatus 20 comprises a motor 60, and controller 33 is configured to rotate the one or more propeller blades 30 by controlling the motor. Alternatively, the one or more propeller blades 30 are rotated without using a motor, such as by a varying magnetic field generated outside the body of the subject, e.g., using techniques described in U.S. Pat. No. 5,762,599 to Sohn, which is incorporated herein by reference.

Apparatus 20 typically does not comprise any sensor of any physiological parameters correlated with a cardiac cycle of the subject.

Apparatus 20 typically does not comprise any sensor of heart rate or the cardiac cycle.

Apparatus 20 further comprises a rotating shaft 36. The one or more propeller blades 30 radiate from rotating shaft 36 (at least when rotated) and are set at a pitch to form a helical spiral, so as to convert rotational motion into linear motion of blood (unlike an impeller, which is a rotor comprising vanes within a pump housing that produces a sucking force).

It is noted that the one or more propeller blades 30 expel the blood in left atrium 32, rather than in a left ventricle 16 of heart 14 (although the blood subsequently flows to left ventricle 16 when mitral valve 44 is open during the cardiac cycle).

The increased pressure above mitral valve 44 augments the left-ventricle filling pressure, thereby increasing filling of left ventricle 16 during diastole. Rotation of the one or more propeller blades 30 gradually builds up pressure above mitral valve 44, beginning during ventricular systole, such that blood flow through the mitral valve is enhanced when the mitral valve opens early in ventricular diastole.

In general, because rotation of the one or more propeller blades 30 push the blood in an inferior direction, the rotation of the one or more propeller blades 30 does not increase pressure at orifices 38 of pulmonary veins, and thus does not contribute to pulmonary edema. Typically, the rotation of the one or more propeller blades lowers pressure at orifices 38 of pulmonary veins, thereby treating pulmonary edema in subjects suffering therefrom.

For some applications, controller 33 is configured to rotate the one or more propeller blades 30 so as to generate a pressure increase of 10-30 mmHg between (a) an inferior area 40 of left atrium 32 between the one or more propeller blades 30 and mitral valve 44 and (b) a superior area 42 of left atrium 32 between the one or more propeller blades 30 and a left atrial roof 46 of left atrium 32. This fairly low pressure increase generally does not result in meaningful backflow.

Optionally, the one or more propeller blades 30 implement at least some of the techniques of the impeller blades described in (a) U.S. Pat. No. 10,039,874 to Schwammenthal et al., including, but not limited to, configurations described therein in which the blades are defined by a frame structure to which a flexible material is attached, and/or (b) PCT Publication WO 2015/177793 to Schwammenthal et al. Both the above-mentioned patent and the above-mentioned publication are incorporated herein by reference.

For some applications, controller 33 is configured to rotate the one or more propeller blades 30 at a speed of at least 100 rpm (e.g., at least 300 rpm, such as at least 500 rpm), no more than 2000 rpm (e.g., no more than 1500 rpm, such as no more than 1200 rpm) 1000 rpm, and/or 100-2000 rpm, e.g., 300-1500 rpm, such as 300-1200 rpm, e.g., 500-1200 rpm, such as 1000 rpm.

For some applications, a circle defined by respective radially-outer ends 50 of the one or more propeller blades 30 when rotating has a diameter of 4-6 cm, such as 5-6 cm. (By contrast, intravascular axial blood flow pumps have substantially smaller diameters, such as less than 2 cm, in order to be implantable in a blood vessel, such as the aorta.)

For some applications, apparatus 20 comprises 2-10 propeller blades 30, such as 2-5 propeller blades, e.g., 3-4 propeller blades.

For some applications, intra-atrial anchor 34 is configured to be disposed entirely within left atrium 32 when anchored therein.

Apparatus 20 is typically not configured to be sealed with respect to mitral valve 44. Typically, intra-atrial anchor 34 is anchored in left atrium 32 such that apparatus 20 is not sealed with respect to mitral valve 44.

For some applications, intra-atrial anchor 34 comprises a stent 52 surrounding the one or more propeller blades 30. Stent 52 comprises a plurality of stent struts arranged so as to define a plurality of stent cells.

Typically, stent 52 is sized and shaped to engage or contact a substantial portion of an interior surface of left atrium 32, and/or to occupy a substantial portion of the volume of left atrium 32. Optionally, stent 52 is generally spherical. Optionally, the one or more propeller blades 30 are disposed generally in a plane at or near an equator 54 of the sphere. For some of these applications, stent 52 is shaped as a cage 56 (scaffolding) surrounding the one or more propeller blades 30. Optionally, cage 56 is contractible during atrial contraction.

For some applications, stent 52 is shaped generally as a complete sphere surrounding the one or more propeller blades. For other applications, stent 52 is shaped generally as a partial sphere, typically subtending at least 3 pi steradians about its center.

For some applications, apparatus 20 comprises a power source 58. Optionally, power source 58 is fully implantable, e.g., comprises a battery. The battery is typically rechargeable, such as wirelessly from outside the body, e.g., by inductive coupling (such as RF inductive coupling). Alternatively, power source 58 is configured to be placed external to the body of the subject, and to wirelessly transmit power.

For some applications, apparatus 20 further comprises an intra-atrial housing 62, which is typically disposed at least partially (e.g., entirely) within stent 52 (e.g., within cage 56). One or more of the following elements, if provided, may be disposed within intra-atrial housing 62: controller 33, power source 58, and motor 60. Rotating shaft 36 extends distally from intra-atrial housing 62.

For some applications, apparatus 20 comprises a subcutaneously-implantable housing ("can") 82 that is configured to be implanted in a subcutaneous pocket, e.g., in the subclavicular space, similarly to a conventional pacemaker pulse generator. In these applications, power source 58 is typically disposed within subcutaneously-implantable housing 82.

For some applications, controller 33 is implantable, such as within intra-atrial housing 62, within subcutaneously-implantable housing 82, or partially within intra-atrial housing 62 and partially within subcutaneously-implantable housing 82 (i.e., controller 33 comprises two portions). For example, controller 33 may be surrounded by stent 52 (e.g., by cage 56) (when controller 33 is disposed within intra-atrial housing 62). For other applications, controller 33 is configured to be disposed external to a body of the subject. For still other applications, a first portion of controller 33 is implantable and a second portion of controller 33 is configured to be disposed external to a body of the subject.

For applications in which apparatus 20 comprises subcutaneously-implantable housing 82, apparatus 20 typically further comprises a lead 80 that electrically couples intra-atrial housing 62 (e.g., controller 33, or a portion thereof, if disposed within intra-atrial housing 62; and/or motor 60, if disposed within intra-atrial housing 62) to subcutaneously-implantable housing 82 (e.g., controller 33, or a portion thereof, if disposed within subcutaneously-implantable housing 82; and/or power source 58, if disposed within subcutaneously-implantable housing 82). For some of these applications, lead 80 passes transseptally from left atrium 32, through an interatrial septum 86, and to a right atrium 88. Lead 80 passes from right atrium 88 using techniques known for placement of a right-atrial pacemaker lead, such as through a superior vena cava (SVC) 90, through one or more veins (such as a subclavian vein, a cephalic vein, and/or an axillary vein), and through a wall of one of the veins. Passing lead 80 through one or more veins benefits from the relatively low pressure of veins.

Reference is still made to FIGS. 1A-B and 2A-B. In an application of the present invention, a method of treating heart failure is provided, the method comprising:

anchoring intra-atrial anchor 34 in left atrium 32 of a subject diagnosed as suffering from heart failure so as to position the one or more propeller blades 30 in left atrium 32 oriented such that the one or more propeller blades 30, when rotated, draw blood from left atrium 32 and expel the blood in left atrium 32 toward mitral valve 44, thereby increasing atrial pressure above mitral valve 44; and activating controller 33 to rotate the one or more propeller blades 30 to produce continuous non-pulsatile blood flow not synchronized with the cardiac cycle of the subject.

For some applications, anchoring intra-atrial anchor in left atrium 32 comprises disposing intra-atrial anchor 34 entirely within left atrium 32.

Figure 3:
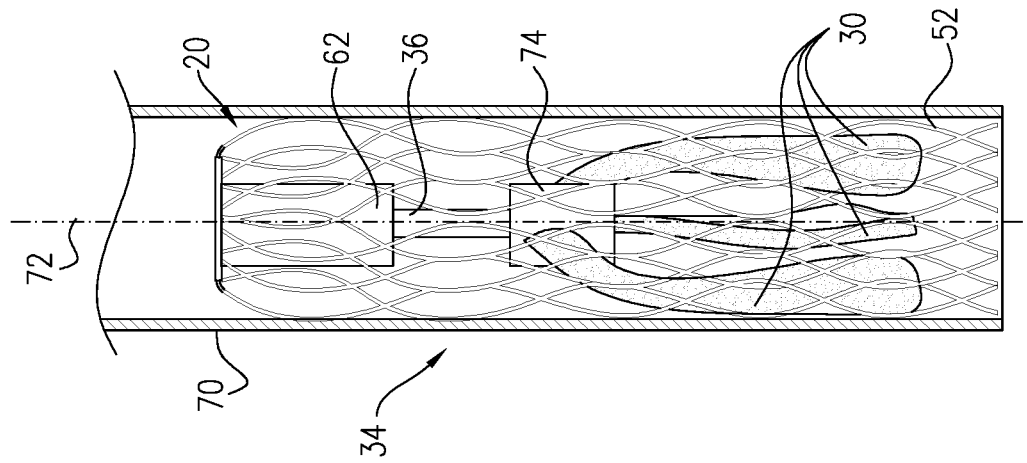
FIG. 3 is a schematic illustration of the apparatus of FIGS. 1A-B in a radially compressed configuration within a sheath, in accordance with an application of the present invention.

Reference is now made to FIG. 3, which is a schematic illustration of apparatus 20 in a radially compressed configuration within a sheath 70, in accordance with an application of the present invention. This radially compressed configuration may be used for transcatheter/transvascular delivery of apparatus 20 to left atrium 32, such as using a transseptal approach, as known in the art.

As can be seen in FIG. 3, stent 52 (e.g., cage 56) is radially compressed (i.e., radially collapsed).

In addition, the one or more propeller blades 30 are radially compressed. For some applications, the one or more propeller blades 30 may be configured to fold toward a central longitudinal axis 72 of apparatus 20 (and sheath 70). For example, the one or more propeller blades 30 may be hingedly coupled to rotating shaft 36, either (a) directly (configuration not shown) or (b) indirectly, by being hingedly coupled to a propeller hub 74 that is coupled to rotating shaft 36 (as shown).

For some applications, the one or more propeller blades 30, when radially compressed (such as by folding), extend distally from rotating shaft 36 (e.g., from propeller hub 74), i.e., in a direction away from intra-atrial housing 62. As a result, the one or more propeller blades 30, when radially compressed, are not disposed alongside rotating shaft 36 or intra-atrial housing 62. Disposal of the one or more propeller blades 30 alongside rotating shaft 36 or intra-atrial housing 62 would increase the diameter of apparatus 20 when disposed in sheath 70, and thus require a larger diameter sheath.

Alternatively, the one or more propeller blades 30, when radially compressed (such as by folding), extend proximally toward intra-atrial housing 62 (configuration not shown).

More than one sheath 70 may be provided; for example, stent 52 (e.g., cage 56) may be disposed in a first sheath, and the other implantable elements of apparatus 20, including the one or more propeller blades 30 may be disposed in a second sheath. The stent is delivered to and deployed in the left atrium using the first sheath, and thereafter the other implantable elements of apparatus 20, including the one or more propeller blades 30, are delivered to the left atrium using the second sheath, and inserted into and coupled to the stent.

For some applications, the one or more propeller blades 30 are configured to expand centrifugally when rotated, and/or one or more springs may be provided to cause the one or more propeller blades to expand radially.

In case of conflict between definitions provided herein and those provided in the patent and patent application publication incorporated herein by reference, the definitions provided herein will prevail.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating heart failure, the apparatus comprising:
   one or more propeller blades;
   a controller, which is configured to rotate the one or more propeller blades to produce continuous non-pulsatile blood flow not synchronized with a cardiac cycle of a subject; and
   an intra-atrial anchor, which comprises a stent surrounding the one or more propeller blades, and which is coupled to the one or more propeller blades and configured to be anchored in a left atrium of the subject so as to position the one or more propeller blades in the left atrium oriented such that the one or more propeller blades, when rotated by the controller, draw blood from the left atrium and expel the blood in the left atrium toward a mitral valve, thereby increasing atrial pressure above the mitral valve,
   wherein the controller is configured to rotate the one or more propeller blades so as to generate a pressure increase of 10-30 mmHg between (a) an inferior area of the left atrium between the one or more propeller blades and the mitral valve and (b) a superior area of the left atrium between the one or more propeller blades and the left atrial roof.

2. The apparatus according to claim 1, wherein the controller is configured to rotate the one or more propeller blades at a speed of no more than 2000 rpm.

3. The apparatus according to claim 2, wherein the controller is configured to rotate the one or more propeller blades at a speed of no more than 1500 rpm.

4. The apparatus according to claim 1, wherein a circle defined by respective radially-outer ends of the one or more propeller blades when rotating has a diameter of 4-6 cm.

5. The apparatus according to claim 1, further comprising a motor, wherein the controller is configured to rotate the one or more propeller blades by controlling the motor.

6. The apparatus according to claim 1, wherein the one or more propeller blades are configured to be folded toward a central longitudinal axis of the apparatus to provide radial compression for delivery to the left atrium, and wherein the one or more propeller blades are configured to expand centrifugally when rotated.

7. The apparatus according to claim 1, wherein the apparatus comprises 2-5 propeller blades.

8. The apparatus according to claim 1, further comprising a power source.

9. The apparatus according to claim 8, wherein the power source is fully implantable.

10. The apparatus according to claim 1, wherein the intra-atrial anchor is configured be disposed entirely within the left atrium when anchored therein.

11. The apparatus according to claim 1, wherein the stent is sized and shaped to engage or contact a substantial portion of an interior surface of the left atrium.

12. The apparatus according to claim 1, wherein the stent is shaped as a cage surrounding the one or more propeller blades.

13. The apparatus according to claim 12, wherein the cage is contractible during atrial contraction.

14. The apparatus according to claim 1, wherein the stent is shaped generally as a complete or partial sphere.

15. The apparatus according to claim 14, wherein the one or more propeller blades are disposed generally in a plane at or near an equator of the complete or partial sphere.

16. The apparatus according to claim 1, wherein the one or more propeller blades and the stent are radially compressible for transcatheter delivery.

17. A system comprising the apparatus according to claim 16, the system further comprising one or more sheaths in which the one or more propeller blades and the stent are disposed radially compressed for transcatheter delivery.

18. The system according to claim 17, wherein the one or more propeller blades are disposed in the one or more sheaths folded toward a central longitudinal axis of the apparatus.

19. The system according to claim 18, wherein the apparatus comprises a rotating shaft, wherein the one or more propeller blades radiate from the rotating shaft when rotated, and wherein the one or more propeller blades are directly or indirectly hingedly coupled to the rotating shaft.

20. The system according to claim 18,
   wherein the apparatus comprises a rotating shaft and an intra-atrial housing disposed at least partially within the stent,
   wherein the rotating shaft extends distally from the intra-atrial housing,
   wherein the one or more propeller blades radiate from the rotating shaft when rotated, and
   wherein the one or more propeller blades, when radially compressed, extend distally from the rotating shaft in a direction away from the intra-atrial housing.

21. A method of treating heart failure, comprising:
   anchoring a stent of an intra-atrial anchor of an apparatus in a left atrium of a subject diagnosed as suffering from heart failure so as to position one or more propeller blades, which are surrounded by the stent, in the left atrium oriented such that the one or more propeller blades, when rotated, draw blood from the left atrium and expel the blood in the left atrium toward a mitral valve, thereby increasing atrial pressure above the mitral valve; and
   activating a controller to rotate the one or more propeller blades:

to produce continuous non-pulsatile blood flow not synchronized with a cardiac cycle of the subject, so as to generate a pressure increase of 10-30 mmHg between (a) an inferior area of the left atrium between the one or more propeller blades and the mitral valve and (b) a superior area of the left atrium between the one or more propeller blades and the left atrial roof.

22. The method according to claim 21, wherein activating the controller comprises activating the controller to rotate the one or more propeller blades at a speed of no more than 2000 rpm.

* * * * *